United States Patent [19]

Cioca

[11] 4,374,121
[45] Feb. 15, 1983

[54] MACROMOLECULAR BIOLOGICALLY ACTIVE COLLAGEN ARTICLES

[75] Inventor: Gheorghe Cioca, Belleville, N.J.

[73] Assignee: Seton Company, Newark, N.J.

[21] Appl. No.: 190,372

[22] Filed: Sep. 24, 1980

Related U.S. Application Data

[63] Continuation-in-part of Ser. No. 74,738, Sep. 12, 1979, Pat. No. 4,279,812.

[51] Int. Cl.$^3$ .............................................. C07G 7/00
[52] U.S. Cl. .................................... 424/19; 424/238; 424/341; 424/116; 424/359; 260/123.7
[58] Field of Search ................ 424/19, 116, 238, 341, 424/359, 360; 256/408; 260/112 R, 123.7; 106/124

[56] References Cited

U.S. PATENT DOCUMENTS

| Re. 26,963 | 10/1970 | Hardy | 424/89 |
|---|---|---|---|
| 2,934,447 | 4/1960 | Highberger | 106/155 |
| 3,435,110 | 3/1969 | Nichols | 424/20 |
| 3,435,117 | 3/1969 | Nichols | 424/271 |
| 3,628,974 | 12/1971 | Battista | 106/125 |
| 3,637,642 | 1/1972 | Fujii | 260/118 |
| 3,939,831 | 2/1976 | Cioca | 128/156 |
| 4,097,234 | 6/1978 | Sohde | 8/94.19 |
| 4,164,559 | 8/1979 | Miyata | 424/14 |
| 4,279,812 | 7/1981 | Cioca | 260/123.7 |

FOREIGN PATENT DOCUMENTS

2319852 10/1973 Fed. Rep. of Germany .

OTHER PUBLICATIONS

Crosby, Research, vol. 15, pp. 427–435, 1962.
Chem. Abst: 92:28614b.

*Primary Examiner*—Allan Lieberman
*Assistant Examiner*—Patricia Short
*Attorney, Agent, or Firm*—Webb, Burden, Robinson & Webb

[57] ABSTRACT

Macromolecular reconstituted collagen is prepared by treating natural insoluble collagen with an aqueous solution comprised of an alkali sulfate salt and an alkali metal hydroxide for at least 48 hours to saponify fats suspended within the natural insoluble collagen. The fat free collagen is then treated with an aqueous solution comprised of an alkali metal sulfate for at least four hours to stabilize the interfibular bonds between individual polypeptide chains. The collagen is then dissolved in an aqueous acid solution and frozen at a rate of $-20°$ C./hour. The frozen collagen is vacuum dried at $10^{-3}$ to $10^{-5}$ torr for at least 16 hours to produce a biologically active collagen article. Various biologically active materials may be added to the aqueous acid solution prior to freezing. The collagen product may then be implanted into an animal or the like and the medication slowly released. The article can remain within the biological system and it will slowly dissolve due to enzymatic digestion and through other biological processes.

5 Claims, No Drawings

MACROMOLECULAR BIOLOGICALLY ACTIVE COLLAGEN ARTICLES

CROSS REFERENCE TO RELATED APPLICATIONS

This application is a continuation-in-part of application Ser. No. 74,738, now U.S. Pat. No. 4,279,812, filed Sept. 12, 1979 entitled "Process for Preparing Macromolecular Biologically Active Collagen."

BACKGROUND OF THE INVENTION

This invention relates to collagen and more particularly to macromolecular reconstituted collagen fiber.

"Natural insoluble collagen" as used herein means and refers to collagen which cannot be dissolved in an aqueous alkaline or in any inorganic salt solution without chemical modification and includes hides, splits, and other mammillian or reptilian coverings. More particularly, "natural insoluble collagen" means and refers to the corium which is the intermediate layer of a bovine hide between the grain and the flesh sides.

Collagen constitutes the connective tissue and is the major type of fibrous protein in higher vertebrae. Collagen in its natural state exists in a triple chain helix along with a constant periodicity between aligned triple chains. The triple helical configuration of collagen is sometimes referred to as a fibril and the fibrils align with an axial periodicity of about 640 Å.

Although there are several types of collagen, the major type is referred to as "type I" which is the major collagen of skin, bones and tendons. The type I collagen has a chain composition of $[\alpha\ 1\ (I)_2\ \alpha\ 2]$. The $\alpha\ 1\ (I)$ and $\alpha\ 2$ chains are homologous.

In young animals there is little intermolecular and interfibrilar crosslinking which provides for some degree of solubility of the collagen. However, during the aging process both intermolecular and interfibrilar crosslinking occurs, thus making the collagen insoluble.

The use of collagen in substantially pure form has been proposed for many uses including for burn dressings as is disclosed in U.S. Pat. Nos. 3,939,831 and 3,514,518, and similar medical applications as is disclosed in U.S. Pat. Nos. 3,157,524 and 3,628,974, along with its use as an additive to food.

While it has been known that collagen can be purified by the depolymerization of natural insoluble collagen along with subsequent reconstitution, the yields have been somewhat low and the resultant product is not necessarily biologically active.

U.S. Pat. No. 3,637,642 is exemplary of a process for dissolving insoluble collagen and regenerating the fiber.

Further, collagen and related materials have found utility in the food, cosmetic and pharmaceutical fields.

Further, methods have been proposed for solubilizing and reconstituting collagen with the use of enzymes to sever intra- and interfibular bonds such as is disclosed in U.S. Pat. No. 3,034,852. Further, processes have been proposed for converting collagen fibrous masses to sheet-like material such as in U.S. Pat. Nos. 2,934,447 and 2,934,446.

According to U.S. Pat. Nos. 3,939,831 and 3,742,955 medicinal dressings can be prepared from collagen having dispersed therein antibiotics and the like to aid in healing of skin which has been burned.

In accordance with the present invention a process for dissolving and regenerating collagen fiber is provided which removes substantially all impurities from the collagen source and provides a substantially pure collagen product which is biologically active and substantially non-antigenic.

BRIEF DESCRIPTION OF THE INVENTION

Macromolecular reconstituted collagen is prepared by treating natural insoluble collagen with an aqueous solution comprised of an alkali sulfate salt and an alkali metal hydroxide for at least 48 hours to saponify fats suspended within the natural insoluble collagen. The fat free collagen is then treated with an aqueous solution comprised of an alkali metal sulfate for at least four hours to stabilize the interfibular bonds between individual polypeptide chains. The collagen is then dissolved in an aqueous acid solution and frozen at a rate of $-18°$ C. to $-24°$ C./hour and preferably $-20°$ C./hour down to a temperature of $-60°$ C. to $-70°$ C. The frozen collagen is vacuum dried at $10^{-3}$ to $10^{-5}$ torr for at least 16 hours to produce a biologically active collagen article. Various biologically active materials may be added to the aqueous acid solution prior to freezing. The collagen product may then be implanted into an animal or the like and the medication slowly released. The article can remain within the biological system and it will slowly dissolve due to enzymatic digestion and through other biological processes.

DETAILED DESCRIPTION OF THE INVENTION

In accordance with the present invention the alkali sulfates useful in the practice of the invention are the alkali metal sulfates such as sodium sulfate, potassium sulfate, and the alkali earth metal sulfates such as calcium sulfate, magnesium sulfate and the like. The most preferred alkali sulfate is sodium sulfate. The alkali metal hydroxides useful in the practice of the invention are sodium and potassium hydroxide, and more preferably, sodium hydroxide. Alkaline earth metal sulfates such as calcium hydroxide and magnesium hydroxide may be substituted in part for the alkali metal hydroxides; however, sufficient potassium and/or sodium hydroxide must be provided.

The aqueous solution of the alkali sulfate and the alkali metal hydroxide is composed of 1 molar to 2.5 molar of alkali metal hydroxide, 0.5 molar to 1 molar of alkali sulfate and 0.1 molar to 0.5 molar of other salt constituents; and more preferably, 2.0 molar to 2.5 molar alkali metal hydroxide, 0.9 molar to 1.0 molar alkali sulfate and 0.1 molar to 0.2 molar of other salt constituents. The alkali metal hydroxide and alkali sulfate should be at an initial pH of about 12 to 13.

The other salt constituents may include alkali metal chloride such as sodium chloride and potassium chloride, alkaline earth metal chlorides such as magnesium chloride, calcium chloride and the like. Care should be taken to properly proportion the alkali sulfate to the alkali metal hydroxide in order to provide for complete saponification of fats suspended within the natural insoluble collagen while retaining the native characteristics of the collagen and controlling the swelling of the collagen fibers. If too much sodium hydroxide is used the collagen will be denatured and intermolecular bonds will be severed. If insufficient sodium hydroxide is used the collagen product will have retained impurities such as fats and other hydrolyzable materials which are undesirable.

In treating the natural insoluble collagen with the aqueous solution of the alkali sulfate salt and the alkali metal hydroxide, the natural insoluble collagen should be cut into pieces which are sufficiently small so that the aqueous solution may penetrate and react therein. The natural collagen pieces should be about ten cubic centimeters or less, and more preferably five cubic centimeters or less. Further, the treatment should take place at ambient temperature for at least 48 hours in order to completely saponify all of the fats suspended within the natural insoluble collagen and to provide a uniform degree of swelling of the collagen fiber. Care should be taken that the initial treatment with the alkali sulfate salt and the alkali metal hydroxide is not too prolonged or the polypeptide chains will be attacked and the collagen will be denatured. For example, when the natural insoluble collagen is cut into pieces of five cubic centimeters the initial treatment should take no more than 96 hours elsewise the collagen fiber will degrade into lower molecular weight components and be denatured. After this initial treatment the natural insoluble collagen becomes very soft and transparent.

After the first treating solution is removed, the collagen is treated with a solution of an alkali metal sulfate or alkali earth metal sulfate or a combination thereof at a substantially neutral pH. The concentration of sulfate should be about 0.5 to 1.0 molar. Other salts such as sodium chloride, potassium chloride, magnesium chloride and the like may be added to this salt treatment so long as a sufficient quantity of alkali metal sulfate, preferably sodium sulfate, is used to stabilize the interfibular bonds of the collagen. This treatment with the alkali metal salt should be for at least four hours.

Preferably the collagen is then neutralized with an aqueous acid solution having a pH between 3 and 4. The acids used to form the aqueous acid solution are typically boric acid, tartaric acid, acetic acid or the like. The washing takes place for about six hours to remove residual salts and base constituents. The pH of the collagen subsequent to neutralization is about seven.

The collagen is then washed with tap water. To remove residual salts within the collagen, it is washed with distilled water several times. Preferably, each washing cycle takes about 4 hours. After each 4 hour cycle the water is decanted and fresh distilled water is added. Normally 4 to 7 cycles are required to remove the residual salts.

The collagen is then dissolved in an aqueous acid solution preferably a solution of 1% to 1.5% by weight collagen is prepared. The acids useful for dissolving the collagen fiber are the weak organic acids such as acetic, citric, lactic, ascorbic and tartaric acids. Preferably the pH is adjusted to below four in order to obtain good solubility. In the case of ascorbic acid a 1% solution is sufficient and in the case of acetic or tartaric acid a 0.5% solution is sufficient. The pH of the aqueous solution should be about 3 to 4.

The collagen solution is then frozen to reduce its temperature at a rate of $-18°$ C. to $-24°$ C./hour until it is at a temperature of $-60°$ C. to $-70°$ C.

The freezing with a temperature reduction of about $-18°$ C. to $-24°$ C./hour is required so that the ice crystals formed are extremely small and do not substantially sever the collagen chains to provide reduced molecular weight to the final collagen product.

To obtain the desired rate of freezing the collagen solution is placed in a freezer at $-60°$ C. to $-70°$ C.

The frozen solution is then placed in a freeze dryer with an initial temperature of $-60°$ C. to $-70°$ C. and vacuum sublimated at $10^{-3}$ to $10^{-5}$ torr. The freeze drying process requires about 12 to 24 hours with a final temperature of 30° C.

In addition, although there is a prevention of extreme destruction of collagen chains by freezing, minor amounts of cryogenic destruction is required in order to form reactive and associative sites which provide cross-linking yielding enhanced mechanical and enzymatic stability to the final product and for combination with other additives to be retained in the collagen.

The collagen prepared in accordance with the invention is one which has a weight average molecular weight of about 450,000 and axial periodicity between triple helix fibrils of about 750 Å to 850 Å and more preferably about 800 Å as opposed to about 640 Å for tropocollagen. Surprisingly, the collagen prepared in accordance with the invention retains substantially the same biological activity as natural collagen which has been purified by long and tedious processes.

The product prepared in accordance with the invention is a spongy tenaceous mass.

Further, the average molecular weight of collagen prepared in accordance with the invention is 383,000 to 460,000 as compared with 300,000 for tropocollagen. The collagen prepared in accordance with the invention has 4 to 6% of the polypeptide chains having a molecular weight of 30,000 to 60,000 and 8 to 12% 1,000,000 to 1,500,000.

In another aspect of the invention biologically active materials may be added to the collagen solution or dispersion prior to freezing. These materials may be drugs or the like. Because the collagen articles produced in accordance with the invention proximate natural or reconstituted collagen, the release of the biologically active material from the collagen approximates the absorption of the material by a biological system which has the collagen implanted or in contact therewith.

It is believed that the severance of polypeptide chains during freezing causes the formation of radicals which associate with particular medicaments and can thus be released in vivo.

Further, after a collagen article having a medicament therein is implanted and the medicament is spent, the collagen article is slowly dissolved and/or decomposed by enzymatic digestion or other biological process thus eliminating the need for removal of the implant.

One particular use of the process of preparing collagen articles useful in the practice of the invention is the blocking of estrus in animals. An appropriate hormone such as chlormadinone acetate, dimethisterone, ethisterone, hydroxyprogesterone, hydroxyprogesterone caproate, medroxyprogesterone, norethindrone, norethynodrel, progesterone, 3-ethylenedioxy, 17-acetoxy, 6-methyl-pregn-5-ene-20-one, and the like, is added to the collagen solution or dispersion prior to freezing. The hormone is added at an effective amount to block estrus preferably at a level of 1 part/40,000 parts of collagen solution to 1 part/50,000 parts of collagen solution.

The collagen article is inserted into the uterus of the animal. After 14 to 18 days the hormone is spent from the collagen article. Two to seven days following the withdrawal of hormone application an enhanced estrus occurs and the animal may then be serviced. Further, the animal may also be artificially inseminated at this time.

In a further embodiment antibiotics such as penicillin, tetracycline, oxytetracycline, chlorotetracycline, chloramphenicol, sulfonamides and the like may be added along with the hormone to prevent infection during insemination and subsequent pregnancy.

Two to fourteen days after insertion of the collagen article, the enzymatic processes in the uterus begins to biochemically degrade the collagen. Glutaraldehyde may be added to the collagen to increase the time required for biochemical degradation.

In another application for using collagen articles prepared in accordance with the invention, a spermicide (such as nonylphenoxy polyoxyethylene ethanol) is added to the collagen solution in the same manner as a hormone is added. The collagen article may be inserted into the vagina and the spermicide kills the sperm injected into the vagina thus preventing conception. The enzymes present in the vagina slowly dissolve the collagen thus removal of the insert is unnecessary. Further, as previously described glutaraldehyde or other cross-linking agents may be added to the collagen to slow the dissolution rate of the collagen in vivo.

A further embodiment of the present invention involves the addition of an antibiotic, a bacteriostat or a bacteriocide to the collagen dispersion of solution prior to freezing. After freeze drying the collagen article may be used for healing of burns or the like.

In general, various medicaments can be added to the collagen dispersion and the collagen article implanted to effect biological, physiological or psychological effects in the biological system in which it is implanted.

The invention will be more fully described with reference to the specific examples herein set forth.

EXAMPLE I

One kilogram of corium derived from raw cow hides is cut into pieces of 5 cm$^3$. The 5 cm$^3$ pieces are treated in a vat with a solution having the following composition:

| Ingredient | Amount |
| --- | --- |
| Water | 3000 ml |
| Calcium hydroxide | 150 g |
| Potassium hydroxide | 50 g |
| Sodium hydroxide | 100 g |
| Sodium sulfate | 144 g |
| Sodium chloride | 100 g |
| Potassium chloride | 200 g |
| Calcium sulfate | 100 g |

The natural insoluble collagen is treated in the above solution with agitation for 48 hours. Observation and testing after treatment showed saponification of all fats and a uniform degree of swelling of the collagen. The corium became very soft, transparent and porous.

The treating vat was drained of the solution and a second solution was charged to the vat having the following composition:

| Ingredient | Amount |
| --- | --- |
| Water | 6000 ml |
| Sodium sulfate | 144 g |
| Sodium chloride | 100 g |
| Potassium chloride | 100 g |
| Calcium sulfate | 100 g |

The corium was treated with the sodium sulfate solution for at least four hours to stabilize the interfibular collagen bonds.

The second solution was drained from the vat by screening and the vat was recharged with a solution of 3000 ml of water and 90 g of boric acid to wash and acidify the twice-treated corium. This treatment took six hours until the collagen had a neutral pH. The collagen was then separated from the liquid and treated with ten liters of tap water for four hours. The tap water was drained and the collagen was again treated with 15 liters of distilled water for at least 4 hours to wash any residual salts therefrom; the water was decanted and 15 liters of distilled water was added. This procedure was repeated until six washing cycles were accomplished. The collagen was dissolved in ten liters of 1% ascorbic acid and stirred until homogeneous. The collagen solution was poured into forms 1 cm high and 2.5 cm in diameter. The forms were frozen at a temperature of $-60°$ C. to $-70°$ C. to effect a temperature reduction rate of the collagen of $-20°$ C./hour to a temperature of $-60°$ C. The collagen was then freeze dried with an initial temperature of $-60°$ C. and a final temperature of 30° C. after 16 hours.

The collagen prepared in accordance with Example I had an average molecular weight of 450,000. The axial period between collagen fibrils was about 800 Å.

The collagen also prepared in accordance with Example I was readily digested by collagenase and upon testing showed no antigenic activity.

The collagen prepared in accordance with Example I had good mechanical properties including elasticity, compressability and softness.

EXAMPLE II

Example I was repeated except that 0.025 grams of medroxyprogesterone acetate was added to 1000 ml of the collagen solution prior to pouring into the forms.

The collagen pellets having the hormone uniformly dispersed therethrough were implanted into the uteri of cows to induce estrus therein. Because of the complexation of the collagen with the hormone the hormone is released over a period of 2 to 14 days. After this period the cows are artificially inseminated. The collagen pellet is allowed to remain in the uterus and slowly dissolves due to enzymatic digestion thereof.

EXAMPLE III

Example II was repeated except that 0.25 grams of chloromycetin was added to the collagen dispersion prior to freezing.

The chloromycetin was effective in preventing infection within the cattle during insemination and subsequent pregnancy.

Although the invention has been described with reference to specific materials and specific times and temperatures, the invention is only to be limited so far as is set forth in the accompanying claims.

I claim:

1. A process of preparing macromolecular reconstituted collagen fiber comprising:
   (a) treating natural insoluble collagen with an aqueous solution comprised of 0.5 to 1 molar of an alkali sulfate salt and 1.0 to 2.5 molar of an alkali metal hydroxide for at least 48 hours and up to 96 hours to saponify fats suspended within the natural insoluble collagen and to uniformly swell the collagen fibers;

(b) treating the fat free collagen with an aqueous solution comprised of an alkali metal sulfate for at least four hours to stabilize the interfibular bonds;
(c) dissolving the collagen in an aqueous solution;
(d) adding an effective amount of a biologically active substance to said solution;
(e) freezing said solution to effect a temperature reduction rate of $-18°$ C. to $-24°$ C./hour to a temperature of $-60°$ C. to $-70°$ C.; and
(f) vacuum drying said solution at $10^{-3}$ to $10^{-5}$ torr for at least 12 hours.

2. The process of claim 1 wherein said biologically active substance is a hormone.

3. The process of claim 1 wherein said biologically active substance is an antibiotic.

4. The process of claim 1 wherein said biologically active substance is a spermicide.

5. The collagen product prepared in accordance with claim 1.

* * * * *